(12) United States Patent
Deitch et al.

(10) Patent No.: US 8,734,337 B2
(45) Date of Patent: May 27, 2014

(54) SURGICAL DEVICE FOR INTERNALLY MANIPULATING AN ORGAN

(71) Applicant: Coloplast A/S, Humlebaek (DK)

(72) Inventors: Sarah J. Deitch, Stillwater, MN (US); Allen Gaynor, Coon Rapids, MN (US); Michael M. Witzmann, Shoreview, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/691,852

(22) Filed: Dec. 3, 2012

(65) Prior Publication Data

US 2013/0274558 A1    Oct. 17, 2013

Related U.S. Application Data

(60) Provisional application No. 61/623,581, filed on Apr. 13, 2012.

(30) Foreign Application Priority Data

Apr. 12, 2012  (DK) ................................ 2012 70182

(51) Int. Cl.
 *A61B 1/32*   (2006.01)
(52) U.S. Cl.
 USPC ........... 600/220; 600/221; 600/222; 600/223; 600/225; 606/90; 606/105
(58) Field of Classification Search
 USPC ..................... 600/220–223, 235; 606/105, 90
 See application file for complete search history.

(56) References Cited

U.S. PATENT DOCUMENTS

| | | |
|---|---|---|
| 832,201 A | 10/1906 | Kistler |
| 1,331,737 A | 2/1920 | Ylisto |

(Continued)

FOREIGN PATENT DOCUMENTS

| | | |
|---|---|---|
| CN | 201179265 | 1/2009 |
| CN | 201481386 | 5/2010 |

(Continued)

OTHER PUBLICATIONS

CooperSurgical; The RUMI II System:The right Choice for all Pelvic Laparoscopic Procedures; Feb. 2011.

(Continued)

*Primary Examiner* — Andrew Yang
*Assistant Examiner* — Olivia C Chang
(74) *Attorney, Agent, or Firm* — Coloplast Corp., Coloplast A/S; Nick Baumann

(57) ABSTRACT

A surgical device includes a rigid shaft connected between a handle and a head. The head of the surgical device is sized for insertion into an organ such as a vagina, a uterus, a rectum, or an esophagus. The head includes an expansion plate and a door coupled to a central plate. The central plate has a distal end connected to the rigid shaft, an anterior surface, and a recess formed in a posterior side of the central plate that provides a posterior surface opposite the anterior surface. The expansion plate is coupled to and movable relative to the anterior surface of the central plate. The door is coupled disposed within the recess of the central plate and movable relative to the posterior surface of the central plate. The expansion plate is movable independently of the door to allow the head to expand and move the organ.

17 Claims, 20 Drawing Sheets

(56) References Cited

U.S. PATENT DOCUMENTS

| | | | |
|---|---|---|---|
| 4,350,251 | A | 9/1982 | Merck |
| 4,638,792 | A | 1/1987 | Burgin |
| 5,113,846 | A | 5/1992 | Hiltebrandt et al. |
| 5,235,966 | A | 8/1993 | Jamner |
| 5,358,496 | A | 10/1994 | Ortiz et al. |
| 5,409,496 | A | 4/1995 | Rowden et al. |
| 5,487,377 | A | 1/1996 | Smith et al. |
| 5,490,819 | A | 2/1996 | Nicholas et al. |
| 5,520,698 | A | 5/1996 | Koh |
| 5,562,680 | A | 10/1996 | Hasson |
| 5,656,012 | A | 8/1997 | Sienkiewicz |
| 5,685,826 | A | 11/1997 | Bonutti |
| 5,716,325 | A | 2/1998 | Bonutti |
| 5,921,996 | A | 7/1999 | Sherman |
| 5,993,461 | A | 11/1999 | Abae |
| 6,048,308 | A | 4/2000 | Strong |
| 6,174,282 | B1 | 1/2001 | Tan |
| 6,183,402 | B1 | 2/2001 | Pedersen et al. |
| 6,379,299 | B1 | 4/2002 | Borodulin et al. |
| 6,582,451 | B1 | 6/2003 | Marucci et al. |
| 6,669,654 | B2 | 12/2003 | Diokno et al. |
| 7,060,029 | B1 | 6/2006 | Hajianpour |
| 7,384,393 | B2 | 6/2008 | Guinan |
| 7,625,377 | B2 | 12/2009 | Veldhuizen et al. |
| 7,654,953 | B2 | 2/2010 | Borodulin et al. |
| 2001/0021854 | A1 | 9/2001 | Donnez et al. |
| 2002/0022771 | A1 | 2/2002 | Diokno et al. |
| 2003/0176883 | A1 | 9/2003 | Sauer et al. |
| 2003/0187334 | A1 | 10/2003 | Biswas |
| 2004/0059362 | A1 | 3/2004 | Knodel et al. |
| 2004/0116955 | A1 | 6/2004 | Foltz et al. |
| 2004/0225196 | A1 | 11/2004 | Ruane |
| 2005/0085827 | A1 | 4/2005 | G. et al. |
| 2005/0182416 | A1 | 8/2005 | Lim et al. |
| 2005/0234294 | A1 | 10/2005 | Saadat et al. |
| 2005/0261683 | A1 | 11/2005 | Veldhuizen et al. |
| 2006/0020271 | A1 | 1/2006 | Stewart et al. |
| 2006/0069436 | A1 | 3/2006 | Sutton et al. |
| 2006/0178562 | A1 | 8/2006 | Saadat et al. |
| 2006/0241652 | A1 | 10/2006 | Doll et al. |
| 2006/0271073 | A1 | 11/2006 | Lam et al. |
| 2007/0027466 | A1 | 2/2007 | Ortiz et al. |
| 2007/0209222 | A1* | 9/2007 | Fischer et al. .................. 33/512 |
| 2007/0249989 | A1 | 10/2007 | Longo et al. |
| 2008/0033471 | A1 | 2/2008 | Paz et al. |
| 2008/0039865 | A1 | 2/2008 | Shaher et al. |
| 2008/0058833 | A1 | 3/2008 | Rizvi |
| 2008/0161825 | A1 | 7/2008 | Greenhalgh et al. |
| 2008/0208210 | A1 | 8/2008 | Blair et al. |
| 2010/0106163 | A1 | 4/2010 | Blair et al. |
| 2010/0114106 | A1* | 5/2010 | Weber .......................... 606/102 |
| 2010/0130817 | A1 | 5/2010 | Conlon |
| 2010/0249498 | A1 | 9/2010 | Wingardner et al. |
| 2010/0280309 | A1 | 11/2010 | Von Pechmann |
| 2010/0280524 | A1 | 11/2010 | Lopez Zepeda |
| 2010/0305578 | A1 | 12/2010 | Auerbach et al. |
| 2011/0034776 | A1 | 2/2011 | Dixon et al. |
| 2011/0259344 | A1 | 10/2011 | Ahluwalia |
| 2011/0306832 | A1 | 12/2011 | Bassan et al. |
| 2012/0016185 | A1 | 1/2012 | Sherts et al. |
| 2012/0041268 | A1 | 2/2012 | Grey et al. |
| 2013/0072749 | A1 | 3/2013 | Fairneny et al. |

FOREIGN PATENT DOCUMENTS

| | | |
|---|---|---|
| KR | 20100122237 | 11/2010 |
| WO | 9324063 | 12/1993 |
| WO | 9400061 | 1/1994 |
| WO | 9603930 | 2/1996 |
| WO | 9811818 | 3/1998 |
| WO | 2005055819 | 6/2005 |
| WO | 08136024 | 11/2008 |
| WO | 2010083836 | 7/2010 |
| WO | 10151429 | 12/2010 |
| WO | 2011044343 | 4/2011 |
| WO | 11082350 | 7/2011 |
| ZA | 200302942 | 6/2004 |

OTHER PUBLICATIONS

Office Action mailed on May 16, 2013 in U.S. Appl. No. 13/705,180.
Office Action mailed on May 16, 2013 in U.S. Appl. No. 13/705,184.
Office Action mailed on May 21, 2013 in U.S. Appl. No. 13/760,074.
Office Action mailed on Jun. 12, 2013 in U.S. Appl. No. 13/553,827.
Extended EP Search Report of Jun. 24, 2013 concerning EP application No. 13159652.0.
Extended EP Search Report of Jun. 24, 2013 concerning EP application No. 13159654.6.
Extended EP Search Report of Jun. 24, 2013 concerning EP application No. 13159653.8.
Advisory Action mailed on Feb. 13, 2014 in U.S. Appl. No. 13/760,074.

* cited by examiner

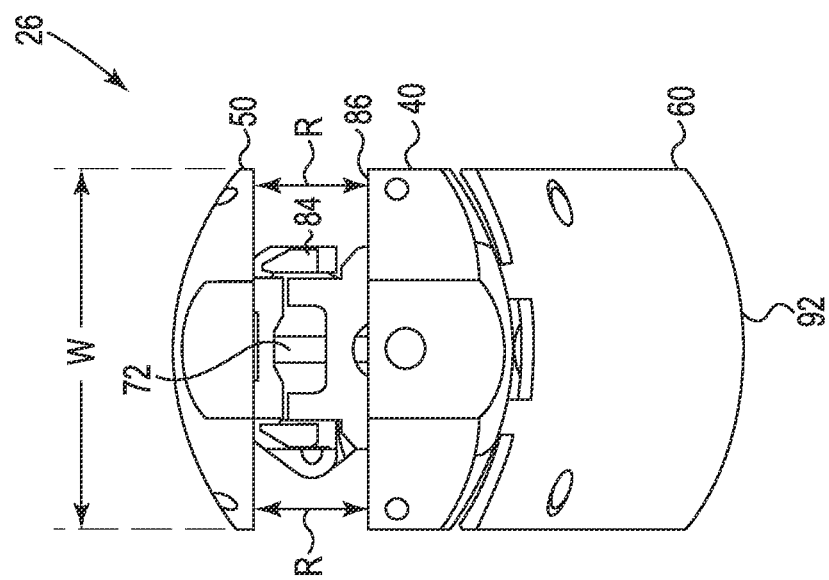

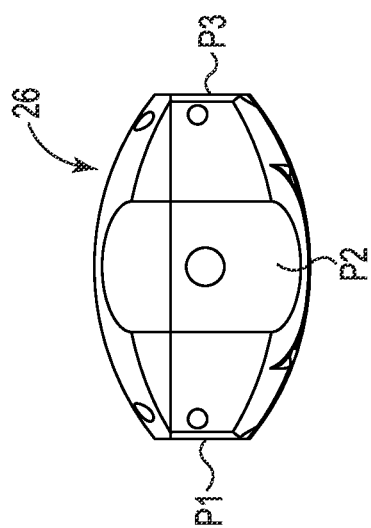

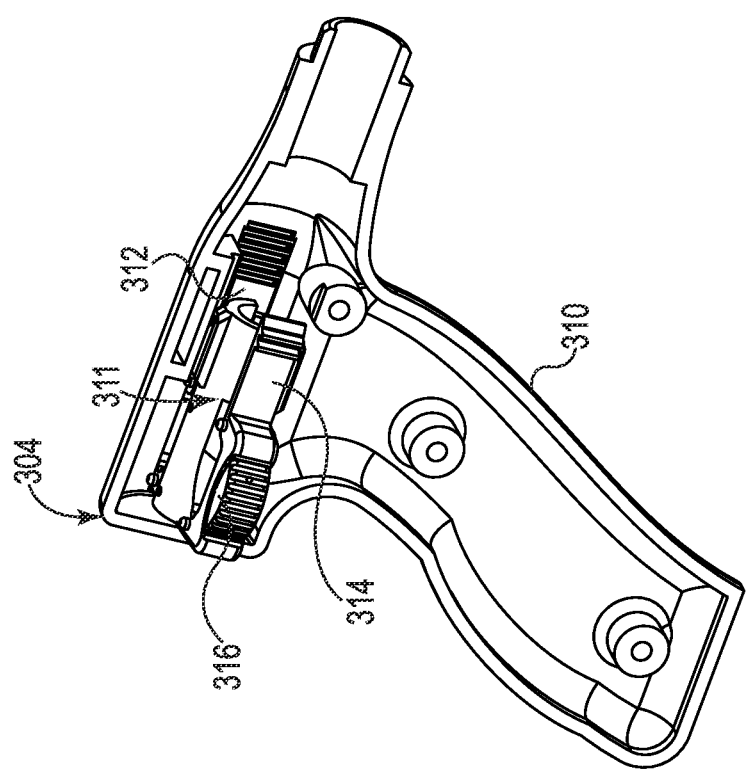

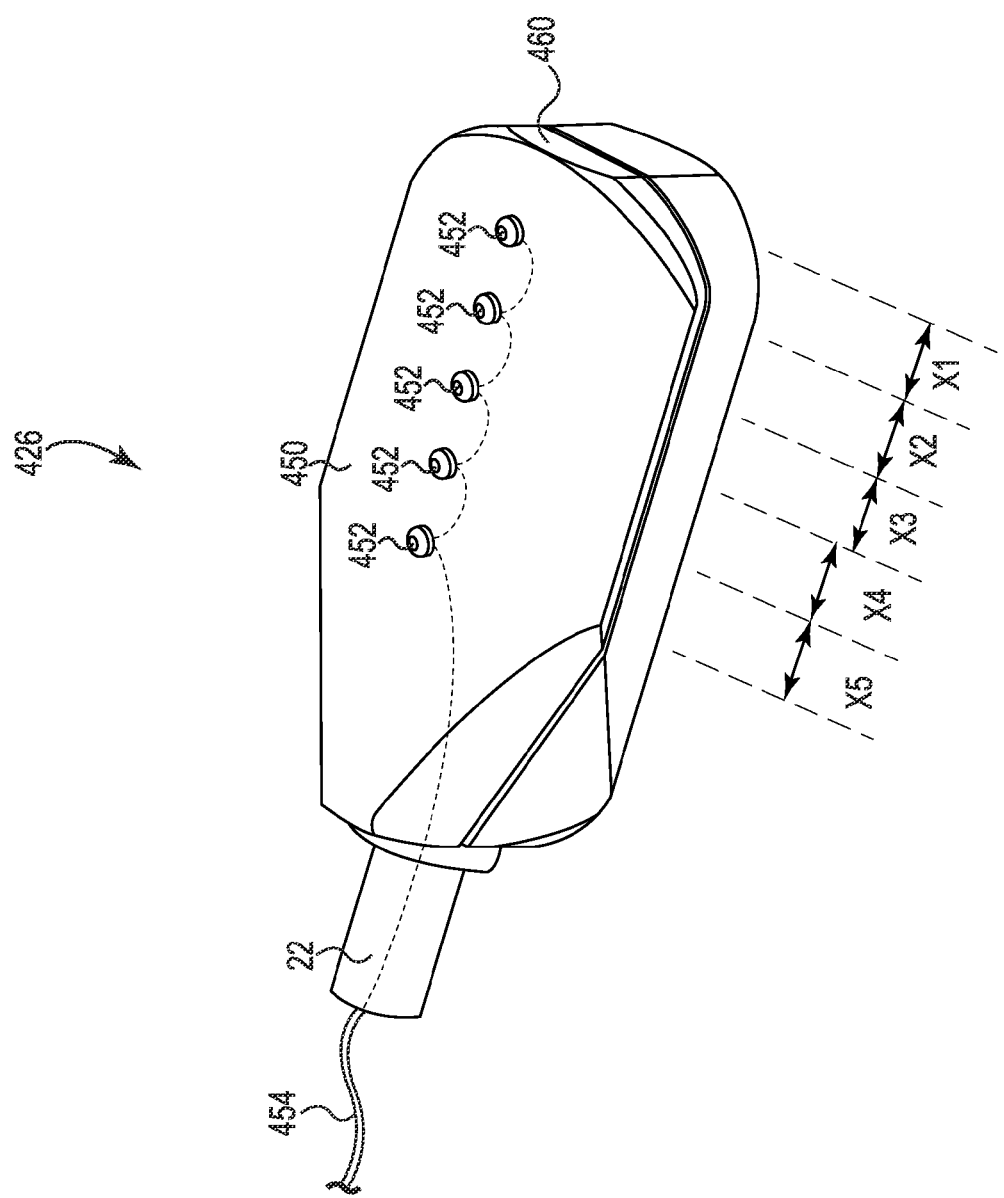

SURGICAL DEVICE FOR INTERNALLY MANIPULATING AN ORGAN

BACKGROUND

There is a trend to move toward minimally invasive surgical procedures that allow the patient to recover faster. Faster recoveries are associated with less time in post anesthesia and other care units, which can translate to a lower cost of patient care.

Many such minimally invasive surgical procedures are performed laparoscopically through multiple access ports formed in the abdomen. At least one access port is formed to provide access for a camera that allows visualization of the internal organs, and at least one access port is formed to provide access for surgical tools to the internal organs. However, it is often the case that the organ selected for surgical intervention will have a surface that is oriented away from the camera such that the surgeon has an imperfect view of the complete organ.

Surgeons would welcome a new device for manipulating the orientation of internal organs to provide a better view of all surfaces of the organ.

SUMMARY

One aspect provides a surgical device. The device includes a rigid shaft connected between a handle and a head. The head of the surgical device is sized for insertion into an organ such as a vagina, a uterus, a rectum, or an esophagus. The head includes an expansion plate and a door coupled to a central plate. The central plate has a distal end connected to the rigid shaft, an anterior surface, and a recess formed in a posterior side of the central plate that provides a posterior surface opposite the anterior surface. The expansion plate is coupled to and movable relative to the anterior surface of the central plate. The door is coupled disposed within the recess of the central plate and movable relative to the posterior surface of the central plate. The expansion plate is movable independently of the door to allow the head to expand and move the organ.

One aspect provides a surgical device including a rigid shaft connected between a handle and a head. The head of the surgical device sized for insertion into a vagina or a rectum and includes a first plate providing an anterior surface and a second plate providing a posterior surface of the head. The second plate is separated from the first plate by a side surface of the head that is separate from the first and second plates. The first plate is movable independently of the second plate to allow the head to expand and move the vagina/rectum.

One aspect provides a surgical device including a rigid shaft connected between a handle and a rigid head. The rigid head of the surgical device sized for insertion into one of a vagina and a rectum and includes a first plate providing an anterior surface and a second plate providing a posterior surface of the rigid head. The second plate is separated from the first plate by a side surface of the rigid head that is separate from the first and second plates. Means are provided for moving the first plate independently of the second plate.

One aspect provides a vaginal manipulator including a shaft connected between a handle and a head. The head includes a central plate having a distal end that is connected to the shaft, an expansion plate coupled to and configured to move radially away from the central plate, and a door having a constrained end and a free end. The constrained end of the door is hinged to the central plate and the free end of the door configured to move away from the central plate. When the vaginal manipulator is inserted into a vagina, the expansion plate is movable relative to the central plate to displace an anterior wall of the vagina and the door is movable relative to the central plate to displace a posterior wall of the vagina into a trans-abdominal line of sight.

One aspect provides a vaginal manipulator including a shaft, a handle connected to a first end of the shaft, and a head connected to a second end of the shaft. The head includes a rigid anterior surface that moves independently from a rigid posterior surface of the head. When the vaginal manipulator is inserted into a vagina, the rigid anterior surface is movable to displace an anterior wall of the vagina and the rigid posterior surface is movable to displace a posterior wall of the vagina. A light source is provided on the head.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 3C is an end view of a head of the surgical device illustrated in FIGS. 1 and 2 showing an extended plate and an extended door.

FIG. 4A is a perspective view and FIG. 4B is an end view of the head of the surgical device illustrated in FIGS. 1 and 2 showing the plate and the door in a retracted state.

FIG. 16 is a cross-sectional view of one embodiment of a handle of an organ expansion device.

FIG. 17 is a perspective view of one embodiment of an organ expansion head of a surgical device.

DETAILED DESCRIPTION

Figure 1:
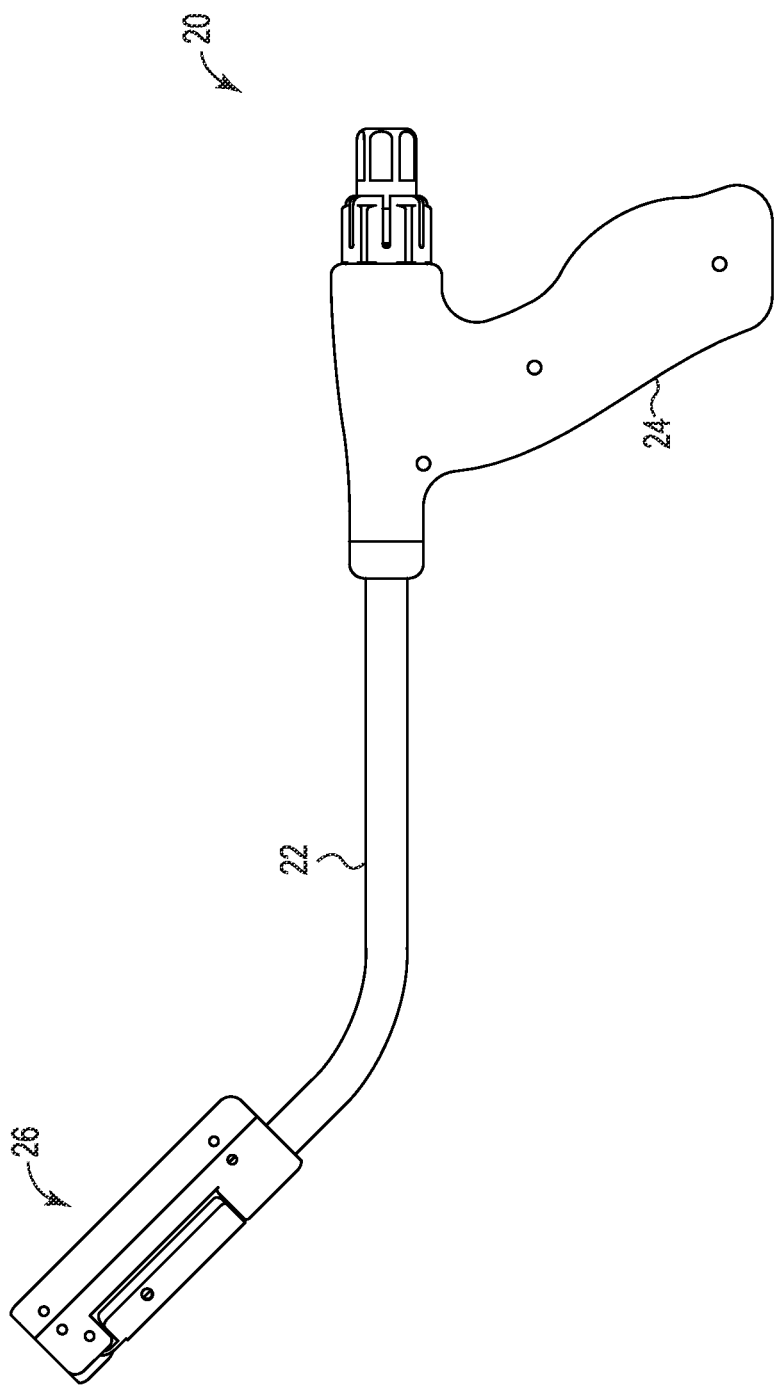
FIG. 1 is a side view of one embodiment of a surgical device.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

Anterior means "forward" or "front," and posterior means "rearward" or "back." Relative to surfaces of an organ in the human body, an anterior surface is oriented forward toward the belly and a posterior surface is oriented rearward toward the spine.

Embodiments provide a surgical device having a head that is insertable into an organ. The head includes at least one expansion plate and at least one pivoting plate that are operable to allow a surgeon to move and orient the organ for improved access to the organ, particularly during minimally invasive surgical procedures. Embodiments of the head include a rigid anterior surface that moves independently from a rigid posterior surface of the head such that when the device is inserted into an organ, the rigid anterior surface is movable to displace an anterior wall of the organ and the rigid posterior surface is movable to displace a posterior wall of the organ. It is particularly useful, for example during a sacrocolpopexy procedure, to move the posterior wall of the organ into a line of sight of a trans-abdominally positioned camera to allow the surgeon to view and manipulate the opposing side of the exterior vaginal wall.

The surgical device is useful in gynecological, colorectal and other procedures. The surgical device may be manually deployed into an organ during an open procedure, or the head of the device may be employed in a laparoscopic procedure or robotically manipulated in a robotically-assisted surgical procedure.

For example, in a laparoscopic procedure a camera system is inserted into a camera port formed through the wall of the abdomen to allow visualization of the internal organs. Other ports are formed in the abdomen to allow tools and devices to access a selected organ. The selected organ will have a surface oriented toward the camera (an anterior surface) and a surface away from the camera (a posterior surface). The head of the surgical device is provided with a first movable surface that operates to move/manipulate the anterior surface of the selected organ. In addition, the head includes a second movable surface that operates to present or displace the posterior surface of the selected organ in a direction for improved visualization by the camera. This feature is particularly useful when manipulating a posterior wall of the vagina that is typically oriented to face away from the abdomen and away from a camera that is inserted into the abdomen laparoscopically.

Embodiments provide an organ expansion device that is useful for manipulating a vagina, a uterus, a rectum, or an esophagus for improved access during minimally invasive surgical (laparoscopic or robotic) procedures.

Embodiments provide surgical device having an organ expansion head that is useful as a vaginal manipulator, which is suitable for use during a laparoscopic or robotic sacrocolpopexy procedure to move the vagina in an anterior direction and/or a posterior direction during tissue dissection and support fixation.

FIG. 1 is a side view of one embodiment of an organ expanding surgical device 20. The organ expanding surgical device 20 (device 20) is insertable into an organ and operable to manipulate or move the organ, or expand a wall of the organ outward, to improve visualization of the organ by a surgeon. The device 20 is suitable for use in expanding and manipulating a variety of organs including, as examples, a vagina (in which the device 20 is termed a vaginal manipulator), a uterus (in which the device 20 is termed a uterine manipulator), a rectum (in which the device 20 is termed a rectal manipulator), or an esophagus (in which the device 20 is termed an esophageal manipulator). The device 20 includes a shaft 22 extending between a handle 24 and a head 26 that is provided with movable surfaces.

In one embodiment, the shaft 22 is a rigid shaft formed from a metal tube, such as stainless steel. In one embodiment, the shaft 22 is substantially straight and is provided without a bend or bend angle. In one embodiment, the shaft 22 includes a bend having an angle in the range from about 5-90 degrees, with one acceptable angle being about 45 degrees as illustrated. The shaft 22 generally encloses portions of an actuator mechanism that extends from the handle 24 to the head 26. In some applications, it is desirable that the shaft 22 is rigid to allow the surgeon to have a one-to-one correlation between movement of the handle 24 and movement of the head 26. In addition, a rigid shaft 22 allows the surgeon to use the device 20 as a lever in moving tissue or in adjusting a location of an organ within the body.

In some applications, the shaft 22 is provided as a flexible shaft that permits movement of the head 26 relative to a fixed position of the handle 24.

The embodiment illustrated in FIG. 1 provides one single rigid shaft 22 connected between the handle 24 and the head 26. In one embodiment, an overall length of the device 20 from a leading end of the head 26 to a trailing end of the handle 24 is in a range between 12-15 inches, with one acceptable overall length for the device of about 13.8 inches (35 cm). The length of the device 20 is thus suitably long enough to accommodate even obese patients.

Figure 2:
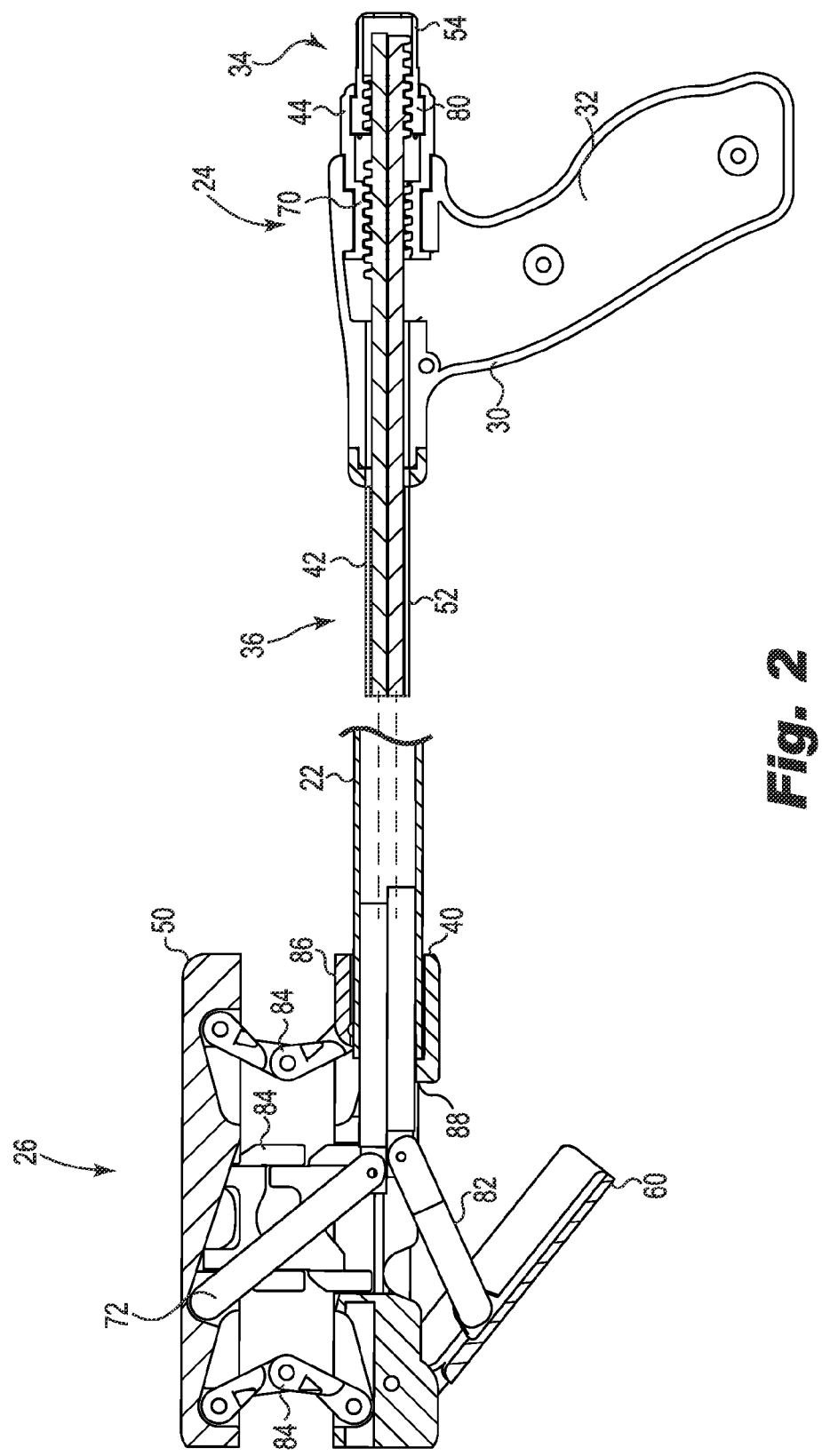
FIG. 2 is a cross-sectional view of one embodiment of the surgical device illustrated in FIG. 1.

FIG. 2 is a partial cross-sectional view of the device 20. In one embodiment, the handle 24 includes a housing 30 that provides a grip 32 and an actuator 34. The housing 30 is suitably provided as a molded plastic or metal structure. In one embodiment, the housing 30 is provided as a two-piece clamshell structure (one piece of which is illustrated in FIG. 2) that is fitted in a mating arrangement around portions of the actuator 34. The length of the housing 30 is elongated to provide a surface that the surgeon may grasp during retroversion of the vagina or other organ.

The actuator 34 is connected to a movement mechanism 36 that is retained within the shaft 22 and extends from the handle 24 to a central plate 40 of the head 26. In one embodiment, the movement mechanism 36 is provided as a split rod having a first rod section 42 coupled between a first knob 44 of the actuator 34 and an expansion plate 50 of the head 26, and a second rod section 52 coupled between a second knob 54 of the actuator 34 and a door 60 of the head 26.

In the exemplary illustrated embodiment, the first rod section 42 is connected to the first knob 44 of the actuator 34 by a thread 70 and to the expansion plate 50 of the head 26 by a link 72. The second rod section 52 is connected to the second knob 54 of the actuator 34 by a thread 80 and to the door 60 of the head 26 by a link 82. In one embodiment, a series 84 of mechanical links is coupled between the central plate 40 and the expansion plate 50, although other assemblies for moving the plate 50 are also acceptable, such as inflatable assemblies and the like.

The shaft 22 is coupled to a distal end of the central plate 40. The central plate 40 has an anterior surface 86 opposite a posterior surface 88. In one embodiment, rotational movement of the first knob 44 displaces the first rod section 42 to move the expansion plate 50 up or down relative to the anterior surface 86 of the central plate 40. In one embodiment, rotational movement of the second knob 54 displaces the second rod section 52 to move the door 60 relative to the posterior surface 88 of the central plate 40. The link 72 and the series 84 of links are provided to allow the expansion plate 50 to move independently of the door 60.

In one embodiment, the actuator 34 provides means for moving the expansion plate 50 independently of the door 60.

In one embodiment, the movement mechanism 36 provides means for moving the expansion plate 50 independently of the door 60.

Figure 3A:
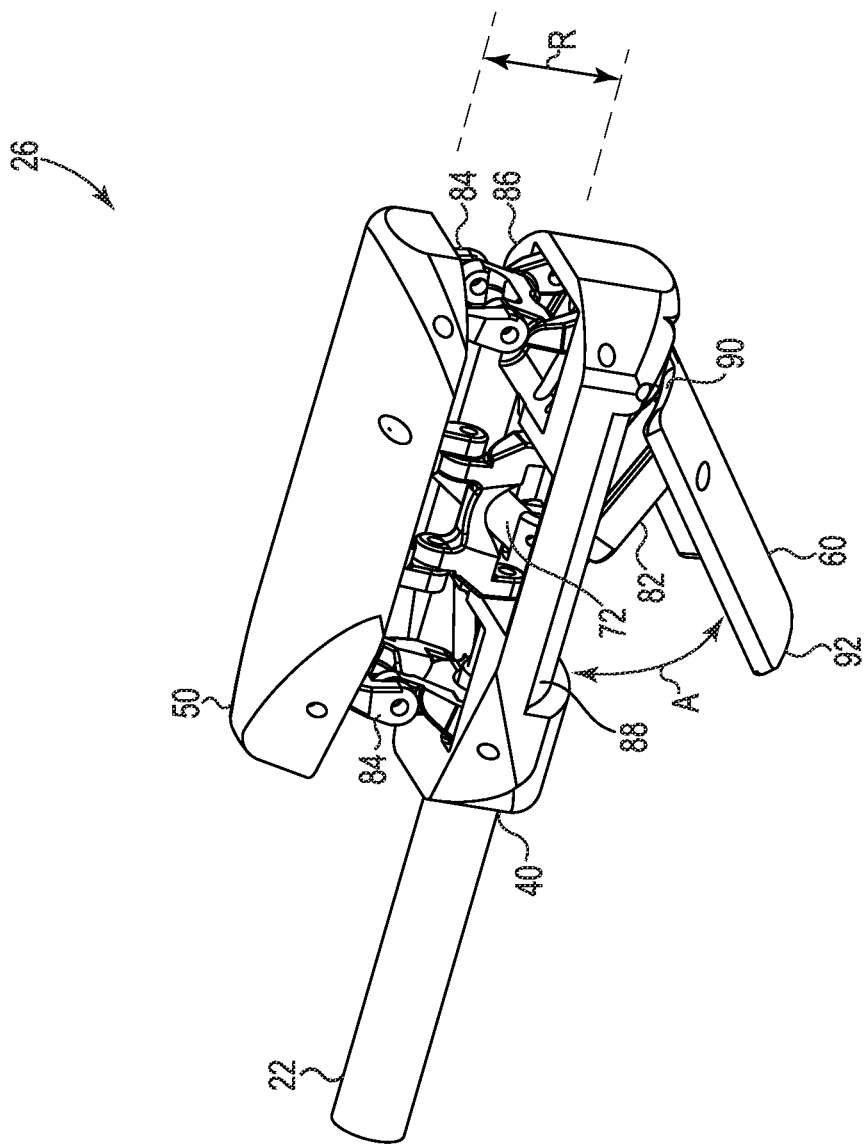
FIG. 3A is a perspective view.
Figure 3B:
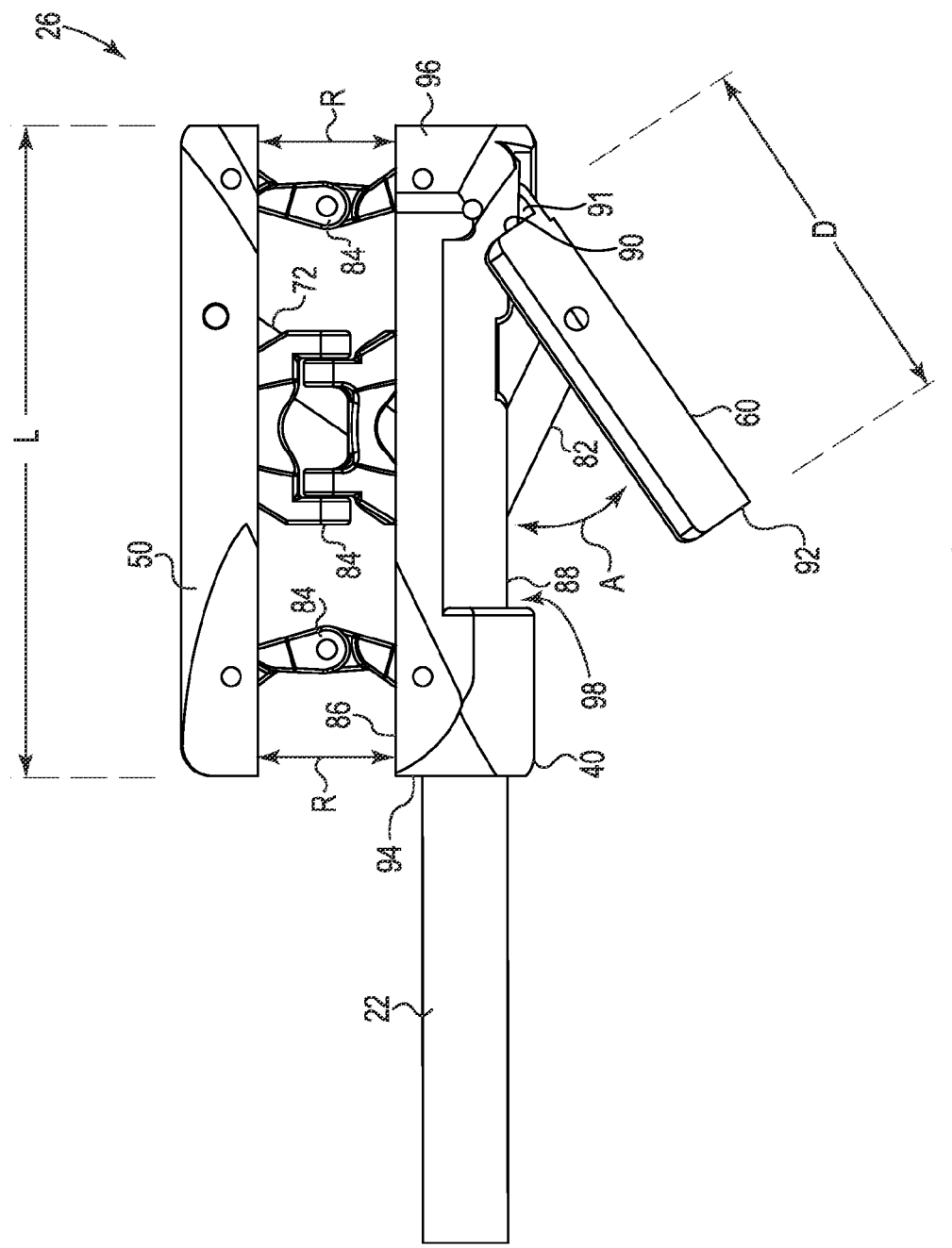
FIG. 3B is a side view.

FIG. 3A is a perspective view, FIG. 3B is a side view, and FIG. 3C is an end view showing the relative movement of the components of the head 26.

FIG. 3A illustrates an embodiment in which the central plate 40 is fixed relative to the rigid shaft 22, the expansion plate 50 is movable relative to the anterior surface 86 of the central plate 40, and the door 60 is movable relative to the posterior surface 88 of the central plate 40. In one embodiment, the expansion plate 50 moves in a radial direction R relative to the central plate 40. The series 84 of links are provided to allow the expansion plate 50 to move in a parallel manner relative to the central plate 40, which is useful when expanding a wall of an organ in an outward direction.

FIG. 3B is a side view of the head 26 with both of the expansion plate 50 and the door 60 in an expanded state. In one embodiment, the door 60 includes a first end 90 that is provided with a hinge 91 that is attached to the central plate 40 and a free end 92 that is not attached to the central plate 40. The first end 90 is constrained by the hinge 91 that is connected to the central plate 40 and the free end 92 is allowed to pivot about the hinge 91. In this manner, the free end 92 of the door is unconstrained and movable in an arc A away from the central plate 40. The door 60 is thus configured as a "kick-out" door that is separate from the expansion plate 50. The free second end 92 of the door 60 is movable outward in the arc A to displace a wall of an organ into a viewing position, where the wall would otherwise be hidden from view from the surgeon.

In one embodiment, the head 26 has a head length L extending from a distal end 94 of the central plate 40 to a proximal end 96 of the central plate 40, and expansion plate 50 has a length that is substantially equal to the head length L. In one embodiment, the central plate 40 includes a recess 98 that defines the posterior surface 88 and the door 60 is sized to fit within the recess 98 of the central plate 40. In one embodiment, the door 60 has a door length D that is less than the head length L.

FIG. 3C is an end view of the head 26 illustrating one embodiment in which both the expansion plate 50 in the door 60 are curved to be convex relative to a longitudinal axis (e.g., an axis into the paper of FIG. 3C) of the head 26. In one embodiment, the expansion plate 50 and the door 60 are provided as continuously solid plates.

With references to FIGS. 3A-3C, the head length L is selected to be long enough to accommodate most dissections, but short enough to accommodate most vaginas. In one embodiment, the head length L is provided in a range between 1-6 inches, preferably the head length L is provided in the range between 2-4 inches, and more preferably the head length L is provided in the range between 2.7-3.5 inches (70-90 mm) One acceptable head length L is 2.7 inches. In one embodiment, the door 60 is provided with a door length D selected to be about 40-80% of the head length L. One acceptable door length D is about 1.6 inches.

The head width W of the head 26 is provided in the range between 1-4 inches and is so selected to be slightly larger than a width of a Y-shaped sacrocolpopexy support fabric identified as Restorelle™ available from Coloplast Corp., Minneapolis, Minn. In one embodiment, the head width W is preferably in a range between 1-2 inches (25-51 mm), and more preferably the head width W is in a range between 1.5-1.58 inches (38-40 mm). The head width W of the head 26 is sized to provide the surgeon with confidence that the support fabric will fit in the location supported by the head 26 without having to trim the fabric or dissect intracorporeally. One acceptable head width W is about 1.6 inches.

The depth of the head 26 between the expansion plate 50 and the door 60 in the closed states is selected to allow the head 26 to be inserted into the entrance of the vagina with no discomfort or a low and acceptable level of discomfort. One acceptable depth for the head 26 when the expansion plate 50 and the door 60 are in the closed states is in a range from 22-28 mm, with one acceptable depth for the head 26 being about 0.9 inches.

Figure 4A:
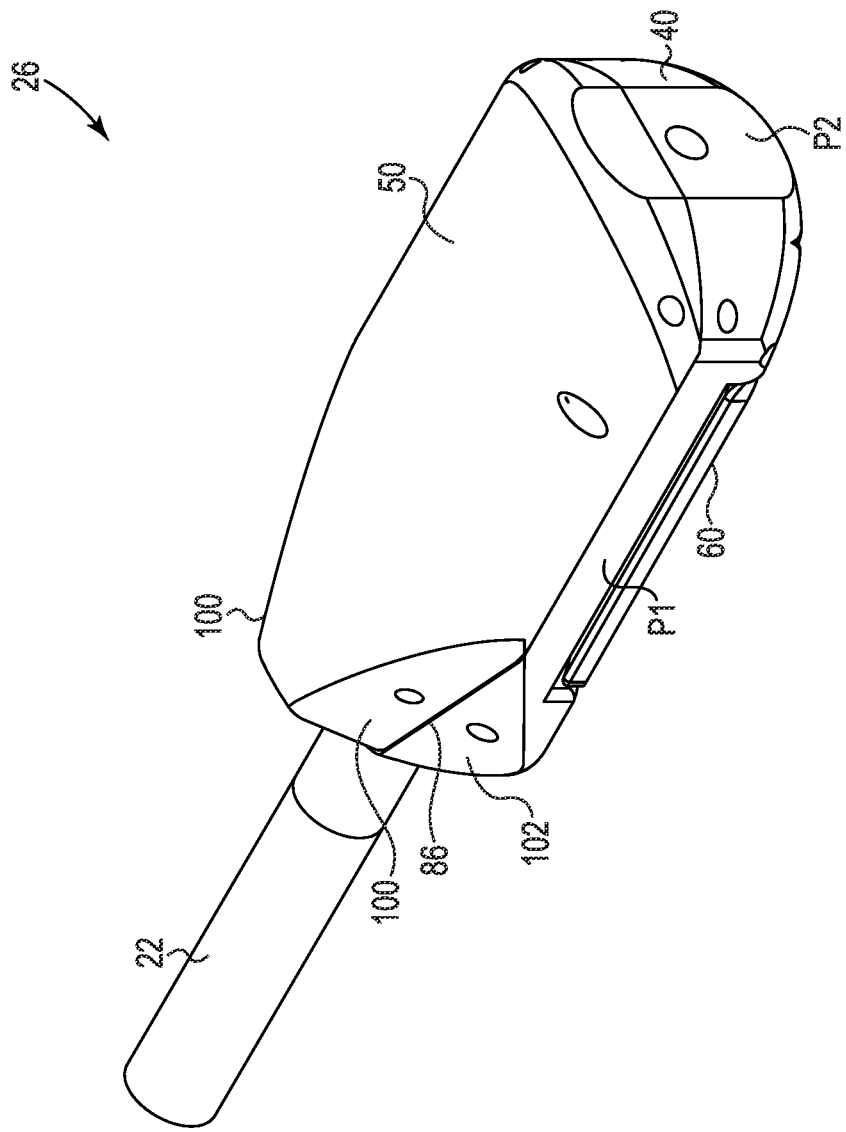

FIG. 4A is a perspective view and FIG. 4B is an end view of the head 26. In one embodiment, a distal end portion 100 (relative to a patient when the head in inserted into the patient) of the expansion plate 50 is tapered to converge toward the shaft 22. The tapered portion 100 of the head 26 provides for pubic bone clearance when the head 26 is first inserted into the pelvis through the vagina, and later as the head 26 is manipulated within the vagina. In one embodiment, a distal end portion 102 of the central plate 40 is also tapered to converge toward the shaft 22 to provide for pubic bone clearance when the head 26 is inserted into the pelvis through the vagina.

In one embodiment, the head 26 is provided with planar sidewalls P1, P2, and P3. The planar sidewalls P1, P2, P3 support the wall of the organ when the head 26 is inserted into the organ, which provides the surgeon with planar work surfaces suitable for the attachment of sutures, dissection, or other surgical intervention. For example, the planar sidewalls P1, P2, P3 present the edges of the vagina better than curved walls, which improve dissection/fixation of the manipulated vagina.

The door 60 provides a second plate that is separated from the expansion plate 50 (or first plate 50) by a side surface provided by the planar surface P1. In this manner, the side surface P1 of the head 26 is separate from the first and second plates 50, 60 and the second plate 60 is separated from the first plate 50 by the side surface P1.

Figure 5:
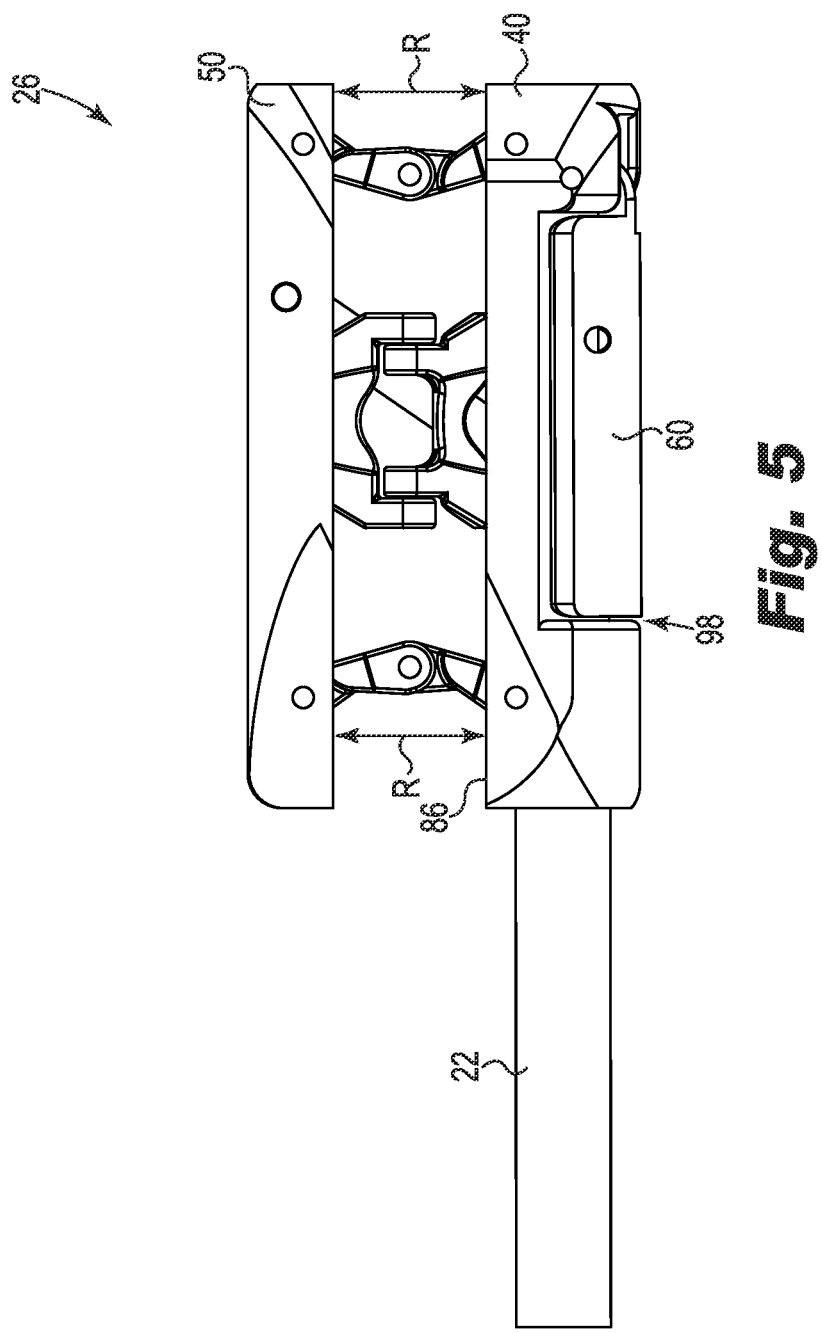
FIG. 5 is a side view of one embodiment of a head of the surgical device illustrated in FIGS. 1 and 2 showing an expanded extension plate.

FIG. 5 is a side view of the head 26 showing the expansion plate 50 moved and elevated away from the anterior surface 86 of the central plate 40. The expansion plate 50 has been extended independently from the door 60 that is secured in the recess 98. The expansion plate 50 has moved radially relative to the longitudinal axis of the shaft 22, in a parallel relationship to the anterior surface 86 of the central plate 40, which allows the expansion plate 52 to elevate or expand a wall of an organ into which the head 26 has been inserted. Elevating the expansion plate 52 positions the wall of the vagina in an orientation that allows the surgeon to suture a support fabric to an exterior of the vagina, for example during a sacrocolpopexy procedure.

Figure 6:
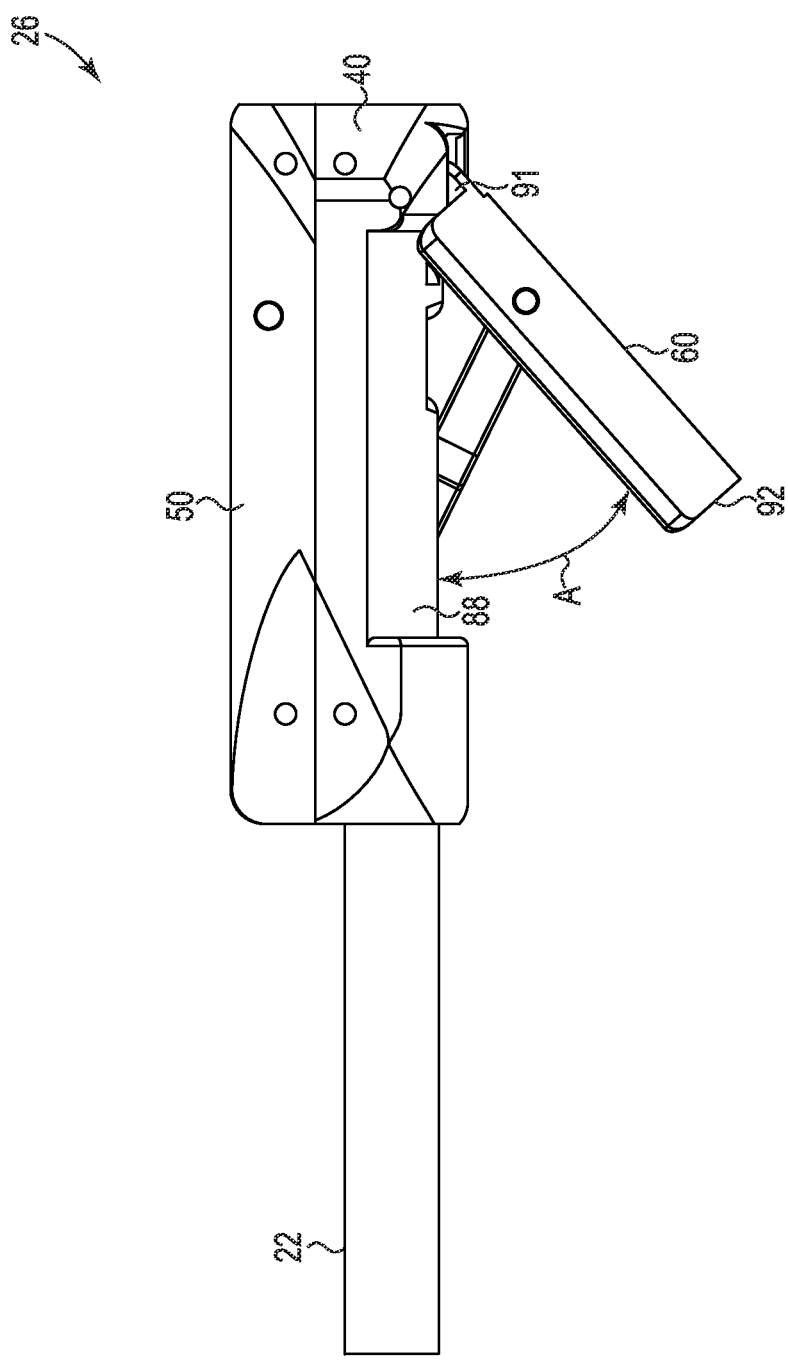
FIG. 6 is a side view of one embodiment of a head of the surgical device illustrated in FIGS. 1 and 2 showing a door displaced away from a central plate.

FIG. 6 is a side view of the head 26 showing the door 60 moved away from a posterior surface 88 of the central plate 40 independently from the expansion plate 50. The free end 92 of the door 60 has pivoted away from the posterior surface 88 of the central plate 40 along the arc A. In this form, the door 60, also termed a kick-out door 60, is structured to selectively present a posterior wall of an organ for viewing by the surgeon where the wall of the organ would otherwise be hidden from view. Pivoting the door 60 about the hinge 91 moves at least a portion of the posterior wall of the organ into the line of sight of the surgeon, for example during a trans-abdominal laparoscopic surgical procedure.

FIGS. 7-12 are schematic views of the device 20 employed to internally manipulate an orientation of the vagina V of the patient during a laparoscopic procedure. FIGS. 7-12 represent the related anatomy but are not drawn to scale. The laparoscopic procedure may be of the robotically-assisted type of laparoscopic procedure. The device is suited for manual use in dissecting tissues off of the vagina V and in manipulating the orientation of the vagina V. Although features of a laparoscopic vaginal procedure are described below, it is to be understood that the device 20 is suitable for manually manipulating the vagina or other organs in other surgical procedures, including other robotic procedures and the like.

Figure 7:
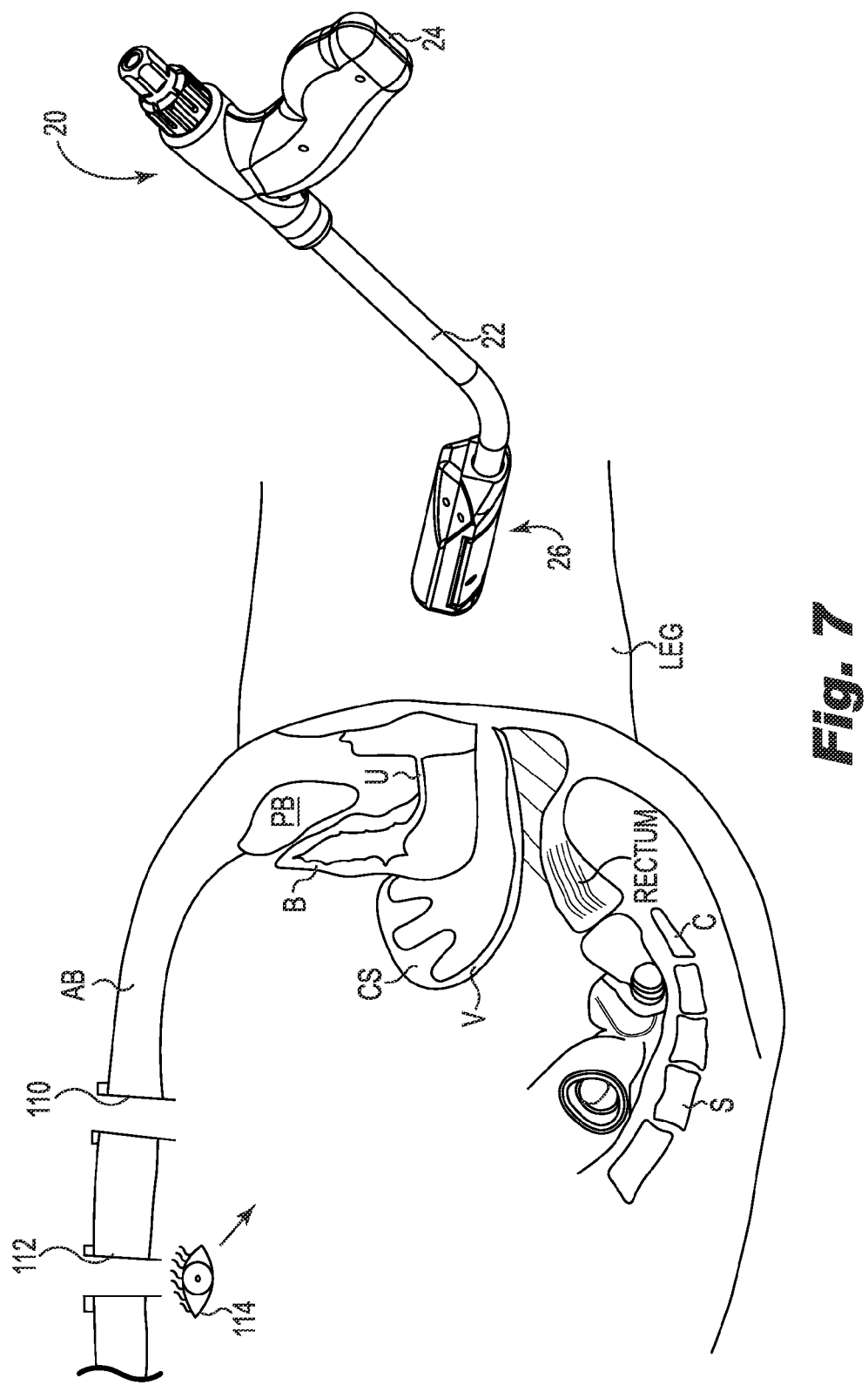
FIG. 7 is a schematic view of the surgical device illustrated in FIG. 1 employed in a laparoscopic surgical procedure.

FIG. 7 is a schematic view of internal organs of a supine patient with the head 26 of the device 20 in position for insertion into the vagina V. A natural vagina has an entrance and terminates at the cervix, which communicates with the uterus. Some women have their uteruses removed through a hysterectomy, and some of these procedures result in the presence of a cervical stump CS connected to the vagina V as illustrated. The bladder B communicates with the urethra U and is located anterior to the vagina V and posterior to the pubic bone PB. The digestive tract and the rectum are located posterior to the vagina V. The sacrum S and the coccyx C are located posterior to the digestive tract. The abdominal wall AB protects and supports the internal organs.

During a laparoscopic surgical procedure, one or more access ports are formed through the abdominal wall AB (usually supported by a trocar) to allow a visualization camera and tools to access the internal organs. In the illustrated embodiment, a first trocar 110 provides an access port for surgical tools and a second trocar 112 provides an access port for an optical camera 114. One or more additional ports (for example a nitrogen inflation port) may be provided through the abdominal wall AB in what is traditionally described as a trans-abdominal approach to the vagina V.

Figure 8:
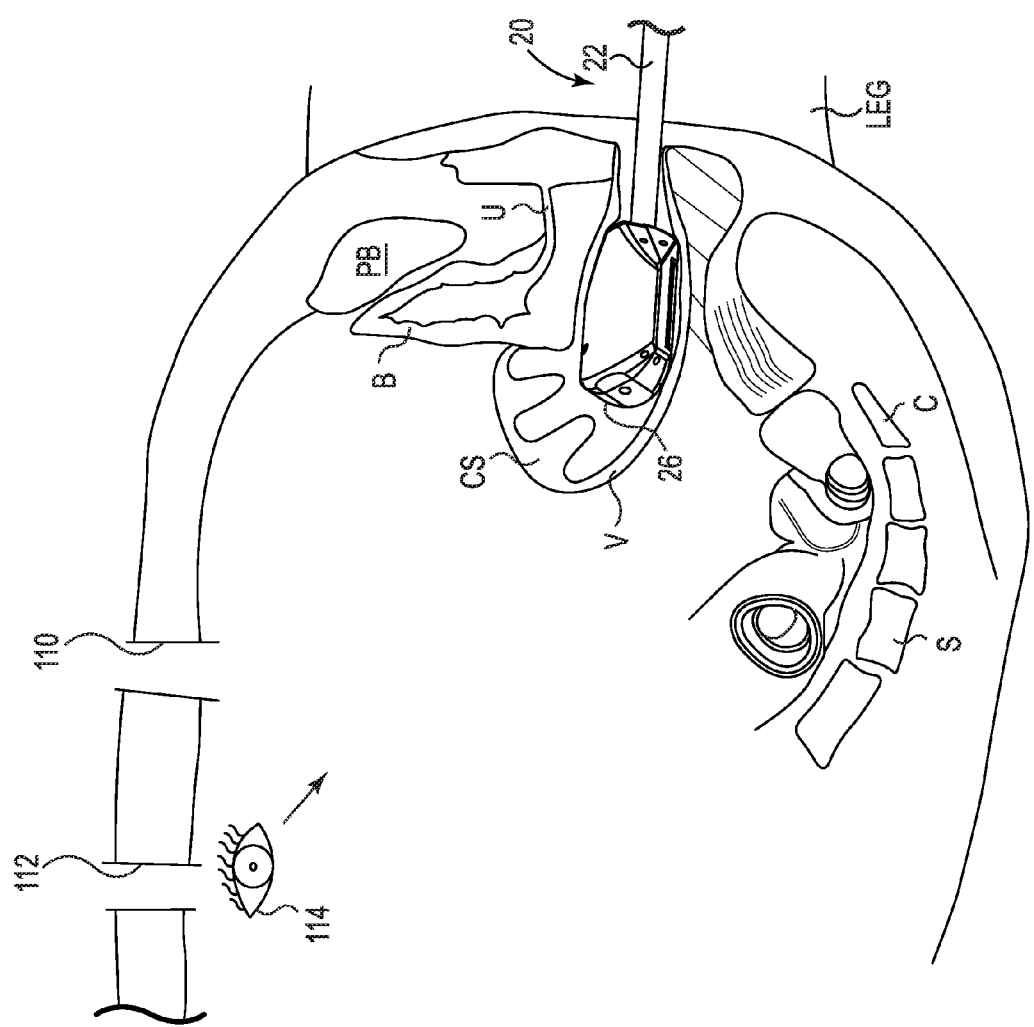
FIG. 8 is a schematic view of the surgical device illustrated in FIG. 7 inserted into a vagina.
Figure 13:
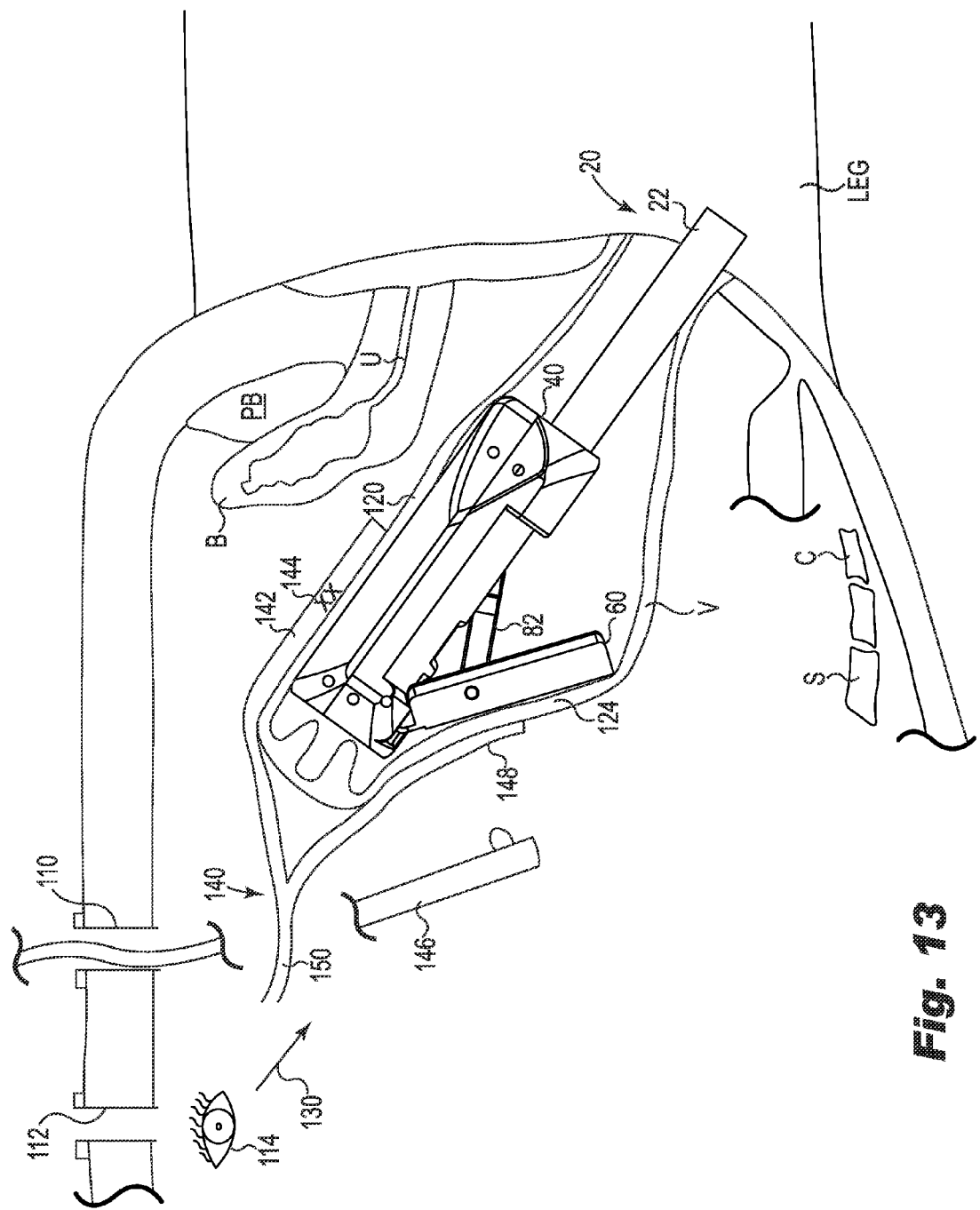
FIG. 13 is a schematic view of the device employed to attach a support to the vagina in a sacrocolpopexy procedure.

FIG. 8 is a schematic view of the head 26 of the device 20 inserted into the vagina V. The shaft 22 is operable to allow the surgeon to manipulate the head 26 and control the orientation of the vagina V, which is useful when dissecting tissues away from the vagina V (FIG. 9) and when attaching support material to the vagina V (FIG. 13). In some embodiments, the shaft 22 is rigid and allows the surgeon to use the shaft 22 as a lever to move and orient the vagina V to assist in tissue dissection or in presenting a wall of the vagina V for visualization by the camera 114. Movement and use of the device 20 is assisted by the camera 114.

Figure 9:
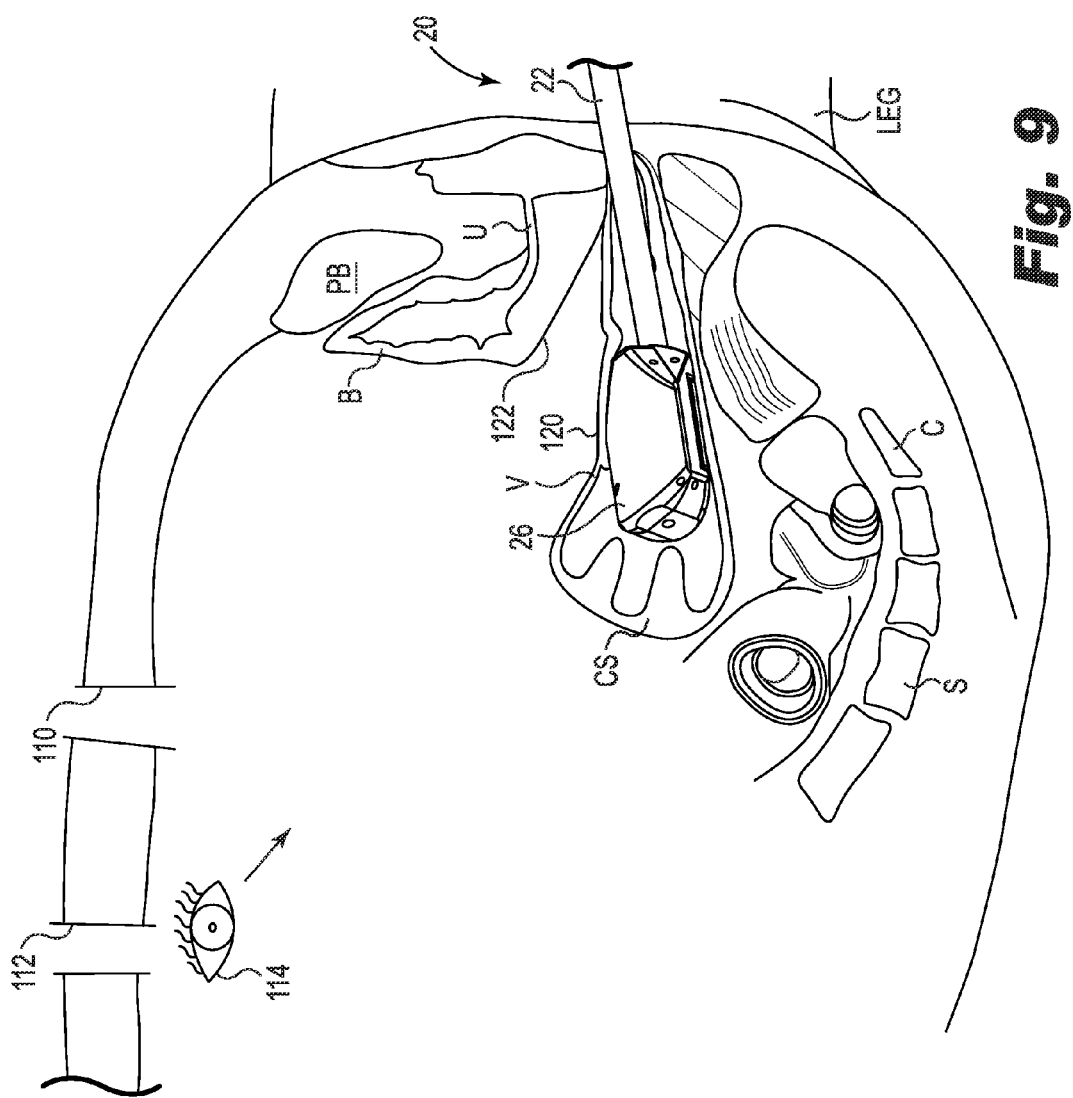
FIG. 9 is a schematic view of the surgical device illustrated in FIG. 7 assisting in the dissection of vesico-vaginal tissue.

FIG. 9 is a schematic view of the device 20 employed to dissect vesico-vaginal tissue away from a wall of the vagina V. One or more surgical tools are inserted through the trocar 110 toward the vagina V. The surgeon moves the head 26 of the device as controlled through the shaft 22 to displace portions of an anterior wall 120 of the vagina, which allows the surgeon to progressively dissect the vesico-vaginal tissue 122 between the bladder B and the anterior wall 120 of the vagina V. It is desirable to expose the anterior wall 120 of the vagina V to allow the surgeon to optimally orient the vagina V when addressing prolapse and in improving support provided to the vagina V, for example during a sacrocolpopexy procedure.

Figure 10:
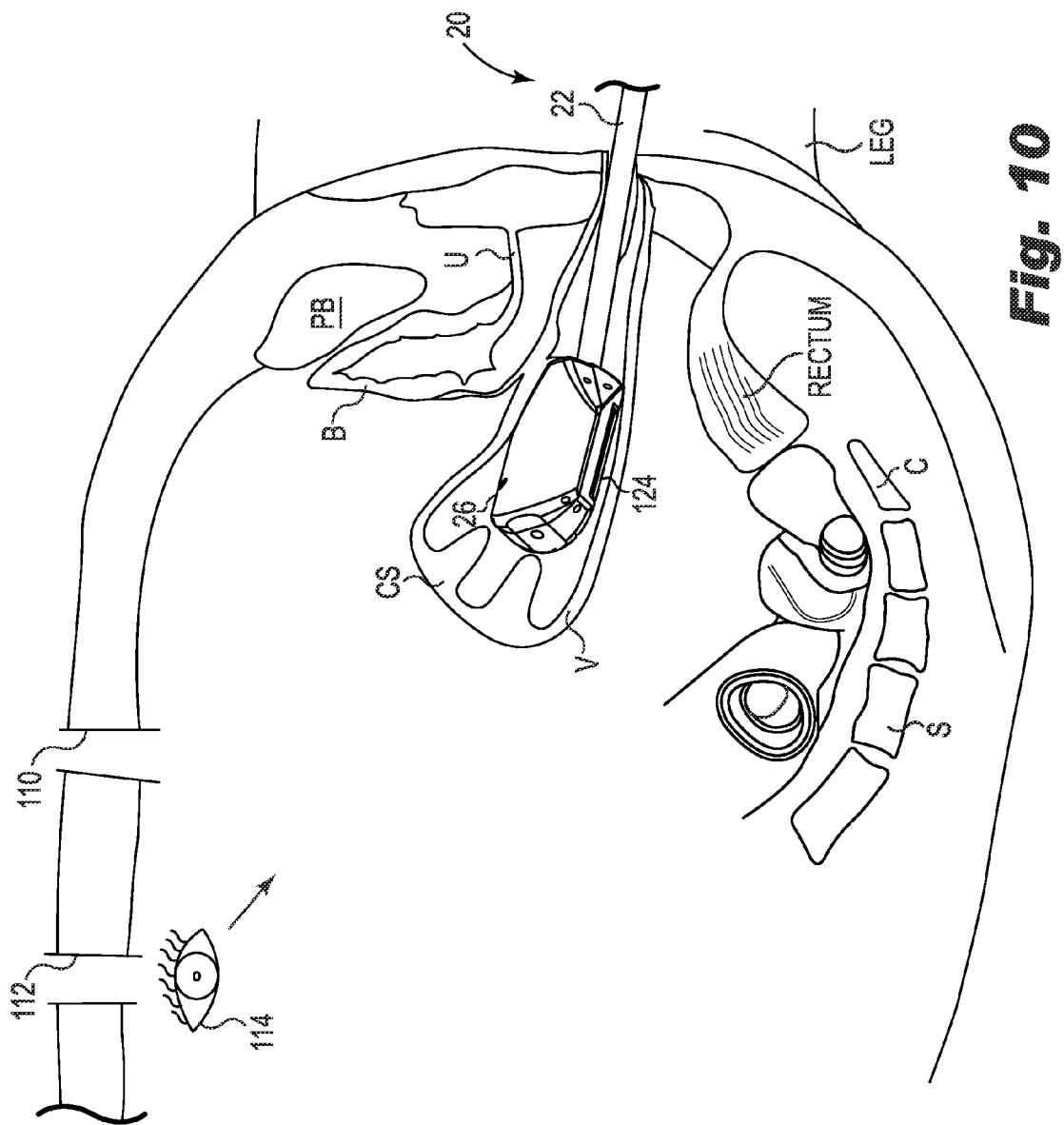
FIG. 10 is a schematic view of the surgical device illustrated in FIG. 7 assisting in the dissection of recto-vaginal tissue.

FIG. 10 is a schematic view of the device 20 employed to dissect recto-vaginal tissue away from a wall of the vagina V. The surgeon employs the shaft 22 to provide a lifting force to the vagina V as suitable other tools are employed to dissect the recto-vaginal tissue from between a posterior wall 124 of the vagina V and a sheath or other tissue layers attached to the rectum. Although not shown, the device 20 is also useful for manipulating the vagina V to allow the surgeon to relieve the uterosacral ligament and to access and relieve other connective tissues attached between the vagina V and other organs.

Figure 11:
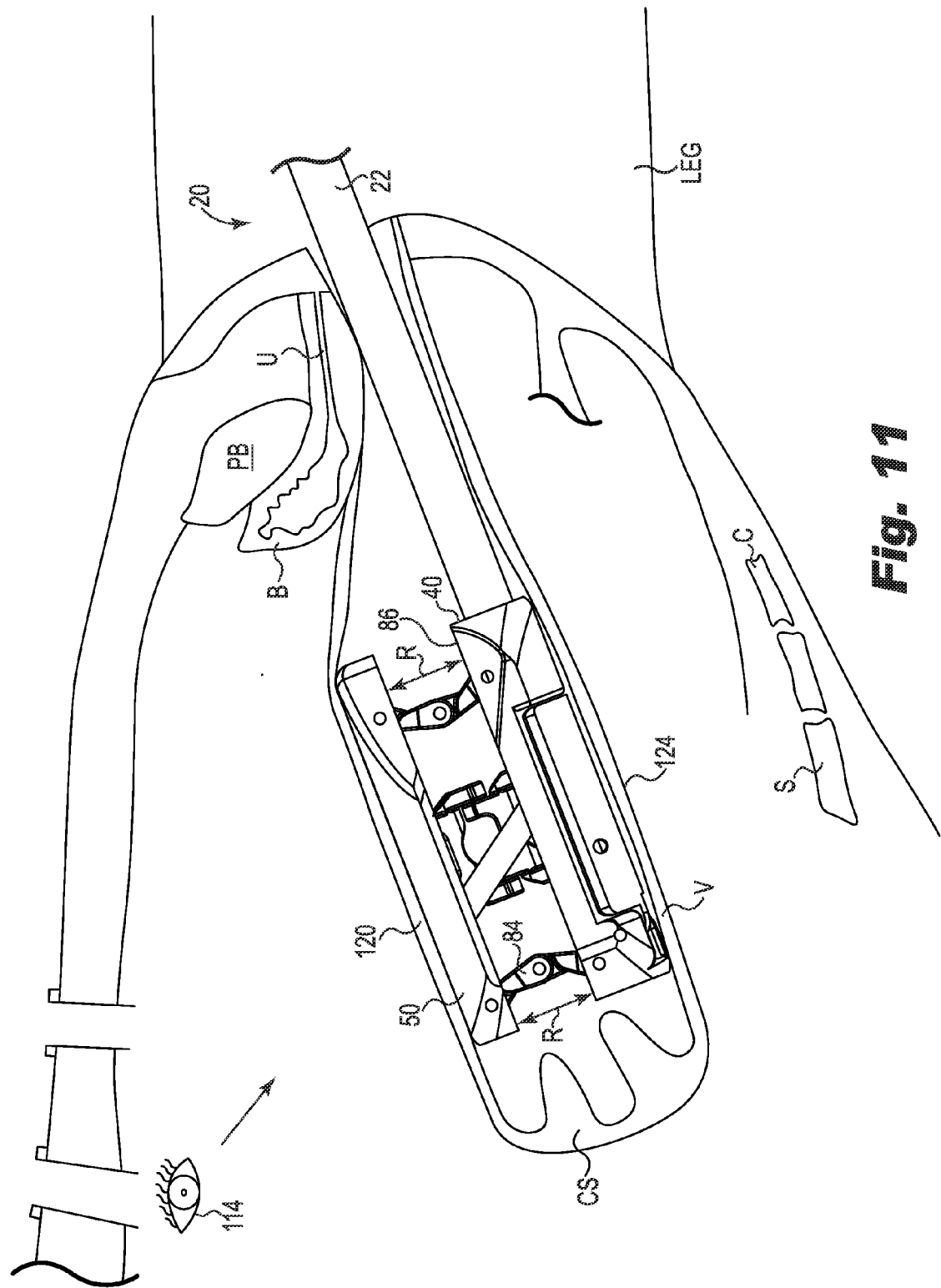
FIG. 11 is a schematic view of an expansion plate of the head of the surgical device illustrated in FIG. 7 extended to provide a view of an anterior wall of the vagina.

FIG. 11 is a schematic view of the vagina V after the anterior wall 120 and the posterior wall 124 of the vagina V have been separated from the bladder/rectal connective tissue, respectively. It is to be understood that other organs and tissue inside of the abdomen can obstruct the surgeon's view of the vagina V. The expansion plate 50 of the device 20 is movable in a radial direction R away from the anterior surface 86 of the central plate 40 to move the anterior wall 120 of the vagina V into a position that provides the surgeon with an improved view of the wall 120 through the camera 114. In addition, the expansion plate 50 provides a backboard or surface that supports the anterior wall 120 of the vagina to allow the surgeon to suture or otherwise surgically intervene in repairing the vagina V.

Figure 12:
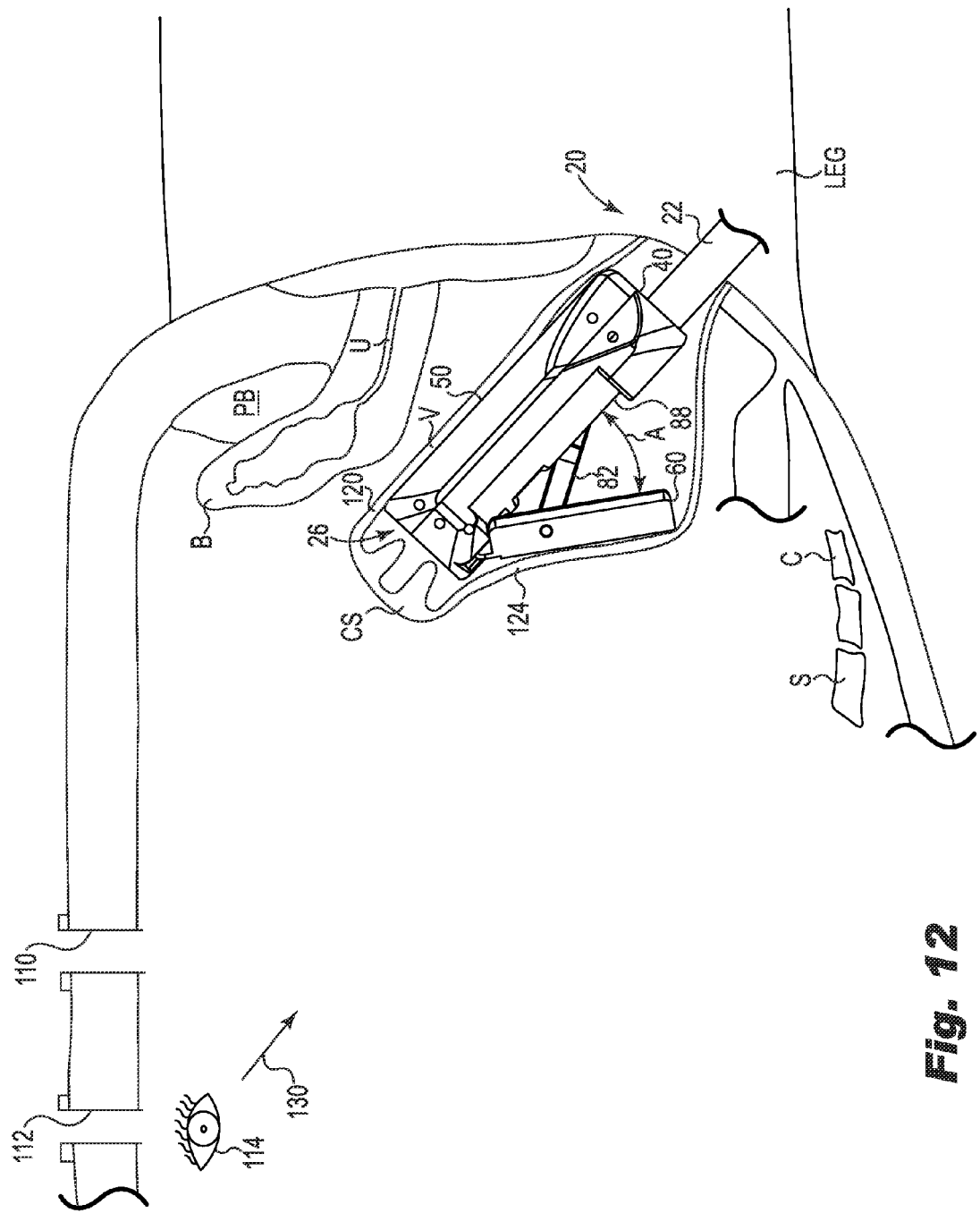
FIG. 12 is a schematic view of a door of the head of the surgical device illustrated in FIG. 7 deployed to provide a view of a posterior wall of the vagina.

FIG. 12 is a schematic view of the vagina after the anterior wall 120 and the posterior wall 124 of the vagina V have been separated from the bladder/rectal connective tissue, respectively.

The posterior wall 124 of the vagina V, and in particular, the distal posterior wall of the vagina V in the direction of the vaginal opening, is typically impeded by other tissues and hidden from the view of the surgeon during laparoscopic surgery. Some tools, such as the uterine manipulator marketed as the RUMI® II System available from Cooper Surgical of Trumbull, Conn., provide a static device that is insertable into the vagina and/or the uterus. Such tools do not provide a view of the distal posterior wall of the vagina V.

In contrast, the plates 50, 60 of the head 26 are independently movable through activation of the actuator 34 and the movement mechanism 36 (see FIG. 2) to provide a fully visible view of all portions of the posterior wall 124 of the vagina V. In the illustrated embodiment, the door 60 has been pivoted away from the posterior surface 88 of the central plate 40 to move (or "kick out") the posterior wall 124 of the vagina V into the line of sight 130 of the camera 114 that is positioned trans-abdominally. The movable plates 50, 60 of the head 26 move independently one from the other to allow the surgeon to advantageously position either the anterior wall 120 or the posterior wall 124 of the vagina V into full visual sight of the camera 114.

FIG. 13 is a schematic view of the device 20 employed to attach a support 140 to the vagina V in a laparoscopically-assisted sacrocolpopexy procedure. One suitable support 140 is a Y-shaped sacrocolpopexy support fabric identified as Restorelle™ available from Coloplast Corp., Minneapolis, Minn. having leg portions 142, 148 diverging away from a tail portion 150.

The patient is prepared for surgery and is usually supine. The access ports are formed in the abdominal wall AB and supported by the trocars 110, 112. The head 26 of the device 20 is inserted into the vagina V to assist in dissecting the vesico-vaginal and recto-vaginal tissues away from the walls 120, 124, respectively, of the vagina V as described above in FIGS. 9-10.

The expansion plate 50 of the device 20 is moved as illustrated in FIG. 11 to assist the surgeon in viewing and attaching the first portion 142 of the support 140 to the anterior wall 120 of the vagina V. In one suitable approach, a number of sutures 144 are placed by a tool 146 controlled by the surgeon to secure the first leg portion 142 of the support 140 to the anterior wall 120 of the vagina V.

The door 60 is movable to orient the posterior wall 124 of the vagina V into the view of the camera 114, which assists the surgeon in attaching the second leg portion 148 of the support 140 to the posterior wall 124 of the vagina, for example through the use of the suture tool 146. The movable plates 50, 60 of the head 26 are useful in orienting the vagina V into a desired support-position as the tail 150 of the support 140 is secured to the sacrum S. The attachment of the support 140 to the vagina V supports and surgically corrects the prolapse of the vagina V, or suitably positions the vagina V into a desired anatomical position after removal of the uterus.

Figure 14:
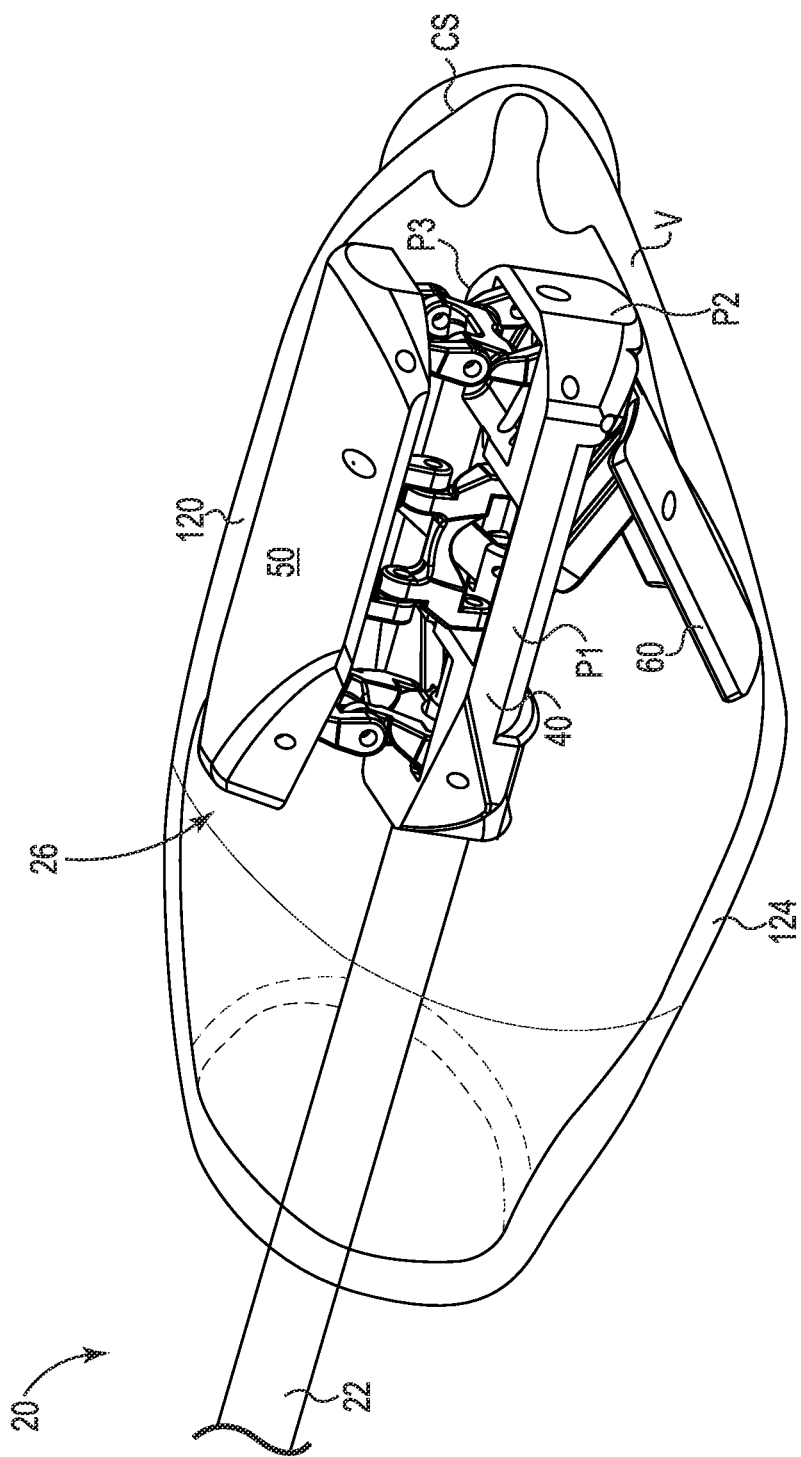
FIG. 14 is a schematic view of the device manipulating the anterior and posterior walls of a vagina.

FIG. 14 is a schematic view of the head 26 of the device 20 employed to independently manipulate, expand, and selectively orient a location of the walls 120, 124 of the vagina V. The expansion plate 50 moves independently of the door 60 to allow the surgeon to move the anterior wall 120 independently from the posterior wall 124 of the vagina V.

In addition, both the expansion plate 50 and the door 60 can be fully extended to essentially "fill" the vagina, which reduces redundant tissue (prevents tissue layers from agglomerating together). The expanded head 26 provides improved sensory feel for the surgeon by applying traction/counter traction to the tissue of the walls 120, 124 of the vagina V.

The planar surfaces P1 and P2 of the head 26 contact the inside of the vagina V to provide a backboard for the walls 120, 124 of the vagina V, and this allows the surgeon to precisely and accurately dissect tissue and apply suture when repairing or supporting the vagina V. With additional reference to FIG. 4B, the planar surfaces P1, P2, P3 provide a planar working back-surface inside of the vagina V that removes the guess-work for the surgeon when incision are made of sutures are placed into the vagina V.

Figure 15:
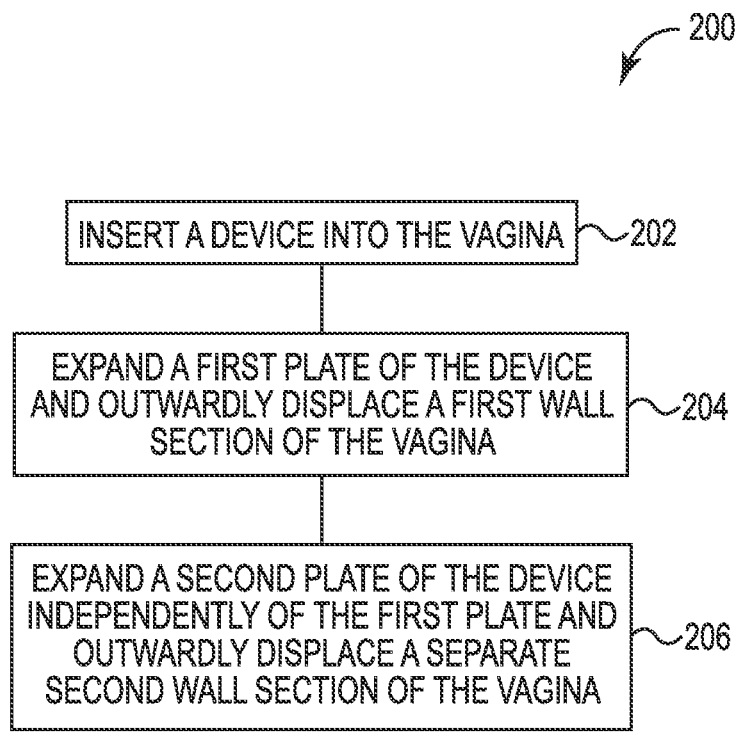
FIG. 15 is a box diagram illustrating a method of surgically supporting a vagina.

FIG. 15 is a box diagram 200 illustrating a method of surgically supporting a vagina. The method includes at 202 inserting a device into the vagina. At 204, a first plate of the device is expanded to outwardly displace a first wall section of the vagina. The method includes at 206 expanding a second plate of the device independently of the first plate to outwardly displace a separate second wall section of the vagina. The method allows manipulation of the vagina by the surgeon to permit selective and independent access and full visibility to both of the anterior wall and the posterior wall of the vagina.

FIG. 16 is a sectional view of one embodiment of a handle 304 suitable for use with the organ expanding surgical device 20 described above. In one embodiment, the handle 304 includes a housing 310 that contains a movement mechanism 311 that connects with the rods 42, 52 (FIG. 2) and is operable to move the plate 50 and the door 60 of the head 26. For example, and with additional reference to FIG. 2, the movement mechanism 311 includes a first slide 312 connected with one of the rods 42, 52 and a second independent slide 314 connected to the other one of the rods 42, 52. Each of the slides 312, 314 is accessed, for example, by a respective button 316 that projects through a wall of the housing 310. Movement of the button 316 moves the slide 314, which moves one of the rods 42, 52 to expand or contract one of the plates 50, 60 of the head 26.

In one embodiment, the movement mechanism 311 provides means for moving the expansion plate 50 independently of the door 60 (see FIG. 14). Suitable movement mechanisms include slides, knobs, triggers, or other activating devices that could be employed to move the expansion plate 50 independently of the door 60.

FIG. 17 is a perspective view of one embodiment of a head 426 suitable for use with the device 20 described above. The head 426 is attached to the shaft 22 and includes an expansion plate 450 similar to the expansion plate 50 described above and a pivoting door (not shown) similar to the door 60 described above. In one embodiment, the expansion plate 450 is provided with a plurality of light sources 452. The light sources 452 are each suitably provided, in one embodiment, as a light emitting diode (LED) that is electrically connected by a wire 454 to a power source (not shown) located in the handle of the device 20. In one embodiment, the door of the head 426 is provided with a plurality of the light sources 452.

Embodiments include at least one brightly illuminating (multi-Watt) light source provided on each major surface (e.g., the anterior side 450 and the opposite posterior side or door) or a plurality of light sources as illustrated. For example, the light source 452 includes a single light source provided on the head 426 and visible through the wall of the vagina to allow a surgeon identify a location on the exterior of the vagina for attachment of support material, or suture, or the like.

In one embodiment, the light source 452 is configured to broadcast light from the head 426 upward into/through the tissue of the vagina V/vaginal vault associated with the cervical stump CS to allow the surgeon viewing from the abdominal side of the tissues to:

1. Assess the thickness of the tissue plane(s), where for example an optically brighter spot would represent a thinner wall of tissue;
2. Assess the health of the tissue planes, for example where differing values of light intensity might indicate different degrees of blood flow within the tissue(s), or innervations, or the like;
3. Better visualize the progress of the tissue dissection undertaken to separate the vagina/bladder and vagina/rectum as described above in FIGS. 9 and 10; and/or
4. Assist the surgeon in measuring the dimensions of the dissected area, for example the light is configurable to both illuminate the surgical area for better vision and transmit through the tissue at pre-determined distances (e.g., four lines or points of light each 1 cm apart).
5. Assist the surgeon in locating a position along the exterior walls of the vagina for the placement of an implantable support. For example, a light source could be located a pre-determined and calculated distance away from a fixed point of the head 426 (such as a leading end), where the light source is configured to be visible through the wall of the vagina to guide the surgeon in placing and fixing the support relative to the vagina.

In one embodiment, each of the light sources 452 is located a selected distance away from an end 460 of the head 426 to provide a visible landmark indicating a pre-determined distance along the head 426. Each light source 452 is configured to be visible through the wall of the vagina, for example as viewed in a trans-abdominal approach, to guide the surgeon in identifying a precise location on the wall of the vagina for placement of a suture or identifying a location on the vagina for dissecting or incising tissue. For example, the tissue of the wall of the vagina will cover the head 426 when the head 426 is inserted into the vagina. Each of the light sources 452 is configured to be illuminated to identify for the surgeon a location that is a pre-determined distance from the end 460 where it might be desired to place a suture or attach a support structure. Each light source 452 is selected to be bright enough to be seen through the relatively thin wall of the vagina, for example when viewed through a camera in a laparoscopic procedure. As opposed to an incandescent light source, the LED light source provides thermally cool light suited for use against tissue.

As one example, a first one of the light sources 452 is located a first distance X1 from the distal end 460 of the head 426, a second one of light sources 452 is located a second distance X2 from X1, a third light source 452 is located a third distance X3 from X2, a fourth light source 452 is located a fourth distance X4 from X3, and a fifth light source 452 is located a fifth distance X5 from X4. In one embodiment, X1=X2=X3=X4=X5 about 1 cm such that the distance X1=1 cm from the distal end 460, the distance X2=2 cm from the distal end 460, and . . . the distance X5=5 cm away from the distal end 460. In one embodiment, each of the distances X1 . . . X5 is selectively pre-determined and the light sources 452 are fabricated into the head 426 to guide the surgeon in suture and support placement onto the wall of an organ into which the head 426 is inserted. The distances X1 . . . X5 need not be equal, for example where X1 is selected to be 1 cm and X2 is selected to be 1.5 cm such that X1+X2=2.5 cm away from the distal end 460.

The light sources 452 are illustrated as provided on the expansion plate 450, although it is to be understood that similar light sources could also be provided on the door 60 (FIG. 3A). That is to say, the light sources 452 could be provided on one or both of the surfaces of the expansion plate 450 and the door 60.

A surgical device has been described that includes a head that is insertable into the organ. The head includes an expansion plate and a pivoting plate that are operable to allow a surgeon to move and orient the organ for improved access to the organ, particularly during minimally invasive surgical procedures.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A surgical device comprising:
 a shaft connected between a handle and a head, the head having a front end portion opposite of a rear end portion that is connected to a second end of the shaft, the head of the surgical device sized for insertion into a pelvic organ selected from the group consisting of a vagina, a uterus, and a rectum, the head comprising:
  a central plate with a distal end connected to the shaft, an anterior surface, and a recess formed in a posterior side of the central plate and providing a posterior surface opposite the anterior surface, and
  a door disposed within the recess of the central plate, with a first end of the door attached by a hinge to the front end portion of the posterior side of the central plate to so configure a free end of the door to be movable away from the rear end portion of the posterior side of the central plate;
 wherein the rear end portion of the head is tapered to provide the head with a tapered rear end portion, the tapered rear end portion of the head has a thickness at each opposed lateral edge of the rear end portion of the head that is less than a thickness of the front end portion of the head and is so configured to provide for pubic bone clearance when the head is inserted into the vagina.

2. The surgical device of claim 1, wherein the device comprises one single rigid shaft connected to the head.

3. The surgical device of claim 1, further comprising: an expansion plate connected to the central plate, the expansion plate is movable radially relative to the anterior surface of the central plate.

4. The surgical device of claim 1, wherein the door is configured to pivot about the first end and the free end of the door is movable in an arc away from the central plate and adapted to displace a wall of the organ.

5. The surgical device of claim 1, wherein both of the first end and the free end of the door fit within the recess.

6. The surgical device of claim 3, wherein the door is provided separate from the expansion plate.

7. The surgical device of claim 3, wherein the expansion plate is a rigid plate.

8. The surgical device of claim 1, wherein the door is a rigid door.

9. The surgical device of claim 1, wherein the handle includes an actuator connected with the door, the actuator movable to move the door.

10. The surgical device of claim 3, wherein the head defines a head length extending from the distal end of the central plate to a proximal end of the central plate and the expansion plate has a length that is substantially equal to the head length.

11. The surgical device of claim 1, wherein the head defines a head length extending from the distal end of the central plate to a proximal end of the central plate and the door has a length that is less than the head length.

12. The surgical device of claim 3, wherein both the expansion plate and the door are curved to be convex relative to a longitudinal axis of the head.

13. The surgical device of claim 12, wherein opposing side walls of the central plate, and the expansion plate, and the door are planar sidewalls.

14. The surgical device of claim 1, wherein the tapered rear end portion of the head has a width at each opposed lateral edge of the rear end portion of the head that is less than a width of the front end portion of the head.

15. A vaginal manipulator comprising:
 a shaft;
 a handle connected to a first end of the shaft; and
 a head having a front end portion opposite of a rear end portion that is connected to a second end of the shaft, the head comprising an anterior surface opposite a posterior surface of the head, the shaft including a curved portion that is configured such that when the vaginal manipulator is inserted into a vagina, the anterior surface of the head is adapted to contact an anterior wall of the vagina and the posterior surface of the head is adapted to contact a posterior wall of the vagina;

wherein the posterior surface of the head includes a recess and a door disposed in the recess, with a first end of the door attached by a hinge to the front end portion of the posterior side of the head to so configure a free end of the door to be movable away from the rear end portion the posterior side of the head;

wherein the recess formed in the posterior surface of the head is sized such that the first end of the door and the free end of the door are configured to fit inside the recess; and wherein the head has a head length extending from a front end of the head to a rear end of the head and the door has a door length that is less than the head length.

16. The vaginal manipulator of claim 15, wherein the rear end portion of the head is tapered to provide the head with a tapered rear end portion, the tapered rear end portion of the head has a thickness at each opposed lateral edge of the rear end portion of the head that is less than a thickness of the front end portion of the head and is so configured to provide for pubic bone clearance when the head is inserted into the vagina.

17. The vaginal manipulator of claim 16, wherein the tapered rear end portion of the head has a width at each opposed lateral edge of the rear end portion of the head that is less than a width of the front end portion of the head.

* * * * *